US012582678B2

(12) United States Patent
Lin et al.

(10) Patent No.: US 12,582,678 B2
(45) Date of Patent: Mar. 24, 2026

(54) METHOD FOR TREATING PLEURAL EFFUSION

(71) Applicant: Hsuan-Ching Tseng, New Taipei (TW)

(72) Inventors: Kun-Cheng Lin, New Taipei (TW); Hsuan-Ching Tseng, New Taipei (TW); Tsai-Wang Huang, Taipei (TW); Ming-Chin Ku, Taipei (TW); Tzu-Li Lin, Taipei (TW); Chen-Yu Lee, Taipei (TW)

(73) Assignee: Hsuan-Ching Tseng, New Taipei (TW)

( * ) Notice: Subject to any disclaimer, the term of this patent is extended or adjusted under 35 U.S.C. 154(b) by 604 days.

(21) Appl. No.: 17/957,677

(22) Filed: Sep. 30, 2022

(65) Prior Publication Data

US 2024/0108659 A1     Apr. 4, 2024

(51) Int. Cl.

| | |
|---|---|
| *A61P 11/00* | (2006.01) |
| *A61K 35/32* | (2015.01) |
| *A61K 36/07* | (2006.01) |
| *A61K 36/076* | (2006.01) |
| *A61K 36/17* | (2006.01) |
| *A61K 36/185* | (2006.01) |
| *A61K 36/232* | (2006.01) |
| *A61K 36/258* | (2006.01) |
| *A61K 36/284* | (2006.01) |
| *A61K 36/31* | (2006.01) |
| *A61K 36/481* | (2006.01) |
| *A61K 36/59* | (2006.01) |
| *A61K 36/61* | (2006.01) |
| *A61K 36/714* | (2006.01) |
| *A61K 36/736* | (2006.01) |
| *A61K 36/756* | (2006.01) |
| *A61K 36/884* | (2006.01) |
| *A61K 36/9068* | (2006.01) |

(52) U.S. Cl.
CPC .............. *A61K 35/32* (2013.01); *A61K 36/07* (2013.01); *A61K 36/076* (2013.01); *A61K 36/17* (2013.01); *A61K 36/185* (2013.01); *A61K 36/232* (2013.01); *A61K 36/258* (2013.01); *A61K 36/284* (2013.01); *A61K 36/31* (2013.01); *A61K 36/481* (2013.01); *A61K 36/59* (2013.01); *A61K 36/61* (2013.01); *A61K 36/714* (2013.01); *A61K 36/736* (2013.01); *A61K 36/756* (2013.01); *A61K 36/884* (2013.01); *A61K 36/9068* (2013.01); *A61P 11/00* (2018.01)

(58) Field of Classification Search
None
See application file for complete search history.

(56) References Cited

U.S. PATENT DOCUMENTS

2004/0086864 A1 *   5/2004   Lo ........................ C12Q 1/6883
                                                            435/6.18
2019/0038698 A1 *   2/2019   Lee ........................ A61K 35/32

FOREIGN PATENT DOCUMENTS

CN        108143989 A   *   6/2018
CN        108310172 A   *   7/2018
CN        112494632 A   *   3/2021

OTHER PUBLICATIONS

Firdaus, M.N.A, et al, Phytochemical and Anti-Inflammatory Potential of *Anredera cordifolia* (Ten): A Review. Journal of Drug Delivery and Therapeutics. Mar. 15, 2022; 12(2);121-125 (Year: 2022).*
English translation of CN10814398A (Year: 2014).*
English translation of CN-112494632-A (Year: 2021).*
English translation of CN-108310172-A (Year: 2018).*
Decoct Definition from Meriam Webster Dictionary (Year: 2025).*
Cleveland Clinic Page on Pleural effusion (Year: 2025).*
Lin, Kun-Cheng, Lee, Chen-Yu, Liao, Yan-Chih, Huang, Tsai-Wang, Clinical case study of TCM treatment for senilel pneumonia, tuberculous accompanied with relapsed pleural effusion and cardiac tamponade (chylopericardium), JCMAS vol. 9 No. 1 Dec. 2021 p. 052-062.

* cited by examiner

*Primary Examiner* — Allison M Fox
*Assistant Examiner* — Marisol Ann O'Neill
(74) *Attorney, Agent, or Firm* — BACON & THOMAS, PLLC

(57) ABSTRACT

A method for treating pleural effusion includes: administering a Chinese medicine composition to a subject in need thereof; wherein, the Chinese medicine composition is an extract of a first mixture comprising *Poria, Polyporus, Rhizoma Alismatis, Atractylodis Rhizoma, Pimenta Officinalis, Zingiberis Rhizoma, Aconiti Lateralis Radix praeparata, Phellodendron amurense, Angelica sinensis, Astragalus Membranaceus, Stephaniae Tetrandrae Radix, Descurainiea Semen, Ephedra Sinica, Armeniacae Semen amarum, Ginseng Radix et Rhizoma, Anredera Cordifolia* and *Velvet Antler.*

9 Claims, No Drawings

METHOD FOR TREATING PLEURAL EFFUSION

BACKGROUND OF THE INVENTION

1. Field of the Invention

The present invention relates to a method for treating pleural effusion. More specifically, the present invention relates to a method for treating pleural effusion with a Chinese medicine composition.

2. Description of Related Art

There are two layers of muscle tissues outside the lungs called the pleura, which are used to regulate the volume expansion and contraction of the thoracic cavity during breathing. The cavity between the two layers of the pleura is called the pleural cavity filled with 5-20 cc of pleural fluid having lubricating or buffering function to protect lungs. It is called pleural effusion when the fluid accumulation in the pleural cavity is higher than the normal level. Severe pleural effusion leads to dyspnea, dry cough or chest pain, and the mortality of repeated pleural effusion is about 77% for cancer, about 29-55% for benign inflammation, about 22-53% for heart failure, and about 14-57% for kidney failure.

At present, the treatment of pleural effusion is mainly based on extraction or drainage of pleural effusion. However, whether it is to extract or drain pleural effusion, it can only be performed on one side at a time. Therefore, it is easy to cause discomfort to the patient suffering from the repeated pleural effusion at left or right side. In addition, the repeated extraction may lead to irreversible lesions even death to the patient.

Therefore, there is a need to provide a therapeutic method to treat, relieve or improve pleural effusion.

SUMMARY OF THE INVENTION

In view of this, the present invention provides a Chinese medicine composition and therapeutic method, which can treat, improve or alleviate pleural effusion.

To achieve the aforementioned object, the present invention provides a Chinese medicine composition, which is an extract of a first mixture comprising *Poria, Polyporus, Rhizoma Alismatis, Atractylodis Rhizoma, Pimenta Officinalis, Zingiberis Rhizoma, Aconiti Lateralis Radix Praeparata, Phellodendron amurense, Angelica sinensis, Astragalus Membranaceus, Stephaniae Tetrandrae Radix, Descurainiea Semen, Ephedra Sinica, Armeniacae Semen amarum, Ginseng Radix et Rhizoma, Anredera Cordifolia* and *Velvet Antler.*

The present invention further provides a method for treating pleural effusion, comprising: administering the aforementioned Chinese medicine composition to a subject in need thereof. In particular, an effective dose of the aforementioned Chinese medicine composition is administered to a subject in need.

In the present invention, the first mixture may comprise 8-22 parts by weight of *Poria*, 6-10 parts by weight of *Polyporus*, 8-22 parts by weight of *Rhizoma Alismatis*, 3-7 parts by weight of *Atractylodis Rhizoma*, 3-7 parts by weight of *Pimenta Officinalis*, 1-5 parts by weight of *Zingiberis Rhizoma*, 1-5 parts by weight of *Aconiti Lateralis Radix praeparata*, 1-5 parts by weight of *Phellodendron amurense*, 0.5-4 parts by weight of *Angelica sinensis*, 8-22 parts by weight of *Astragalus membranaceus*, 3-12 parts by weight of *Stephaniae Tetrandrae Radix*, 6-22 parts by weight of *Descurainiea Semen*, 0.5-4 parts by weight of *Ephedra Sinica*, 1-5 parts by weight of *Armeniacae Semen amarum*, 1-10 parts by weight of *Ginseng Radix et Rhizoma*, 1-5 parts by weight of *Anredera Cordifolia* and 0.1-3 parts by weight of *Velvet Antler*. Preferably, the first mixture may comprise 9-21 parts by weight of *Poria*, 7-9 parts by weight of *Polyporus*, 9-21 parts by weight of *Rhizoma Alismatis*, 4-6 parts by weight of *Atractylodis Rhizoma*, 4-6 parts by weight of *Pimenta Officinalis*, 2-4 parts by weight of *Zingiberis Rhizoma*, 2-4 parts by weight of *Aconiti Lateralis Radix Praeparata*, 2-4 parts by weight of *Phellodendron amurense*, 1-3 parts by weight of *Angelica sinensis*, 9-21 parts by weight of *Astragalus Membranaceus*, 4-11 parts by weight of *Stephaniae Tetrandrae Radix*, 7-21 parts by weight of *Descurainiea Semen*, 1-3 parts by weight of *Ephedra Sinica*, 2-4 parts by weight of *Armeniacae Semen amarum*, 2-9 parts by weight of *Ginseng Radix et Rhizoma*, 2-4 parts by weight of *Anredera Cordifolia* and 0.5-2 parts by weight of *Velvet Antler.*

In an embodiment of the present invention, the first mixture may comprise 8-12 parts by weight of *Poria*, 6-10 parts by weight of *Polyporus*, 8-12 parts by weight of *Rhizoma Alismatis*, 3-7 parts by weight of *Atractylodis Rhizoma*, 3-7 parts by weight of *Pimenta Officinalis*, 1-5 parts by weight of *Zingiberis Rhizoma*, 1-5 parts by weight of *Aconiti Lateralis Radix praeparata*, 1-5 parts by weight of *Phellodendron amurense*, 0.5-4 parts by weight of *Angelica sinensis*, 8-12 parts by weight of *Astragalus Membranaceus*, 3-7 parts by weight of *Stephaniae Tetrandrae Radix*, 6-10 parts by weight of *Descurainiea Semen*, 0.5-4 parts by weight of *Ephedra Sinica*, 1-5 parts by weight of *Armeniacae Semen amarum*, 1-5 parts by weight of *Ginseng Radix et Rhizoma*, 1-5 parts by weight of *Anredera Cordifolia* and 0.1-3 parts by weight of *Velvet Antler*. Preferably, the first mixture may comprise 9-11 parts by weight of *Poria*, 7-9 parts by weight of *Polyporus*, 9-11 parts by weight of *Rhizoma Alismatis*, 4-6 parts by weight of *Atractylodis Rhizoma*, 4-6 parts by weight of *Pimenta Officinalis*, 2-4 parts by weight of *Zingiberis Rhizoma*, 2-4 parts by weight of *Aconiti Lateralis Radix praeparata*, 2-4 parts by weight of *Phellodendron Amurense*, 1-3 parts by weight of *Angelica sinensis*, 9-11 parts by weight of *Astragalus membranaceus*, 4-6 parts by weight of *Stephaniae Tetrandrae Radix*, 7-9 parts by weight of *Descurainiea Semen*, 1-3 parts by weight of *Ephedra Sinica*, 2-4 parts by weight of *Armeniacae Semen Amarum*, 2-4 parts by weight of *Ginseng Radix et Rhizoma*, 2-4 parts by weight of *Anredera Cordifolia* and 0.5-2 parts by weight of *Velvet Antler.*

In an embodiment of the present invention, the first mixture may comprise 13-17 parts by weight of *Poria*, 6-10 parts by weight of *Polyporus*, 13-17 parts by weight of *Rhizoma Alismatis*, 3-7 parts by weight of *Atractylodis Rhizoma*, 3-7 parts by weight of *Pimenta Officinalis*, 1-5 parts by weight of *Zingiberis Rhizoma*, 1-5 parts by weight of *Aconiti Lateralis Radix praeparata*, 1-5 parts by weight of *Phellodendron amurense*, 0.5-4 parts by weight of *Angelica sinensis*, 13-17 parts by weight of *Astragalus membranaceus*, 6-10 parts by weight of *Stephaniae Tetrandrae Radix*, 13-17 parts by weight of *Descurainiea Semen*, 0.5-4 parts by weight of *Ephedra Sinica*, 1-5 parts by weight of *Armeniacae Semen amarum*, 3-7 parts by weight of *Ginseng Radix et Rhizoma*, 1-5 parts by weight of *Anredera Cordifolia* and 0.1-3 parts by weight of *Velvet Antler*. Preferably, the first mixture may comprise 14-16 parts by weight of *Poria*, 7-9 parts by weight of *Polyporus*, 14-16 parts by weight of *Rhizoma Alismatis*, 4-6 parts by weight of *Atractylodis Rhizoma*, 4-6 parts by weight of *Pimenta Officinalis*, 2-4 parts by weight of *Zingiberis Rhizoma*, 2-4 parts by weight of *Aconiti Lateralis Radix Praeparata*, 2-4 parts by weight of *Phellodendron amurense*, 1-3 parts by weight of *Angelica sinensis*, 14-16 parts by weight of *Astragalus Membranaceus*, 14-16 parts by weight of *Stephaniae Tetrandrae Radix*, 14-16 parts by weight of *Descurainiea Semen*, 1-3 parts by weight of *Ephedra Sinica*, 2-4 parts by weight of *Armeniacae Semen amarum*, 4-6 parts by weight of *Ginseng Radix et Rhizoma*, 2-4 parts by weight of *Anredera Cordifolia* and 0.5-2 parts by weight of *Velvet Antler*.

In an embodiment of the present invention, the first mixture may comprise 18-22 parts by weight of *Poria*, 6-10 parts by weight of *Polyporus*, 18-22 parts by weight of *Rhizoma Alismatis*, 3-7 parts by weight of *Atractylodis Rhizoma*, 3-7 parts by weight of *Pimenta Officinalis*, 1-5 parts by weight of *Zingiberis Rhizoma*, 1-5 parts by weight of *Aconiti Lateralis Radix praeparata*, 1-5 parts by weight of *Phellodendron amurense*, 0.5-4 parts by weight of *Angelica sinensis*, 18-22 parts by weight of *Astragalus membranaceus*, 8-12 parts by weight of *Stephaniae Tetrandrae Radix*, 18-22 parts by weight of *Descurainiea Semen*, 0.5-4 parts by weight of *Ephedra Sinica*, 1-5 parts by weight of *Armeniacae Semen amarum*, 6-10 parts by weight of *Ginseng Radix et Rhizoma*, 1-5 parts by weight of *Anredera Cordifolia* and 0.1-3 parts by weight of *Velvet Antler*. Preferably, the first mixture may comprise 19-21 parts by weight of *Poria*, 7-9 parts by weight of *Polyporus*, 19-21 parts by weight of *Rhizoma Alismatis*, 4-6 parts by weight of *Atractylodis Rhizoma*, 4-6 parts by weight of *Pimenta Officinalis*, 2-4 parts by weight of *Zingiberis Rhizoma*, 2-4 parts by weight of *Aconiti Lateralis Radix Praeparata*, 2-4 parts by weight of *Phellodendron amurense*, 1-3 parts by weight of *Angelica sinensis*, 19-21 parts by weight of *Astragalus Membranaceus*, 9-11 parts by weight of *Stephaniae Tetrandrae Radix*, 19-21 parts by weight of *Descurainiea Semen*, 1-3 parts by weight of *Ephedra Sinica*, 2-4 parts by weight of *Armeniacae Semen amarum*, 7-9 parts by weight of *Ginseng Radix et Rhizoma*, 2-4 parts by weight of *Anredera Cordifolia* and 0.5-2 parts by weight of *Velvet Antler*.

The Chinese medicine composition of the present invention is prepared by the following steps: providing the first mixture; mixing the first mixture with water to form a second mixture; heating the second mixture to obtain the Chinese medicine composition. In addition, a crude extract may be obtained after heating the second mixture; and, a liquid extract may be kept after filtering the crude extract, thereby obtaining the Chinese medicine composition.

In the present invention, the part by weight is 2.5-5 gram per part, preferably 3-4 gram per part, more preferably 3.75 gram per part.

In the present invention, the "pleural effusion" includes transudative pleural effusion, exudative pleural effusion, or a combination thereof, but the present invention is not limited thereto. Usually, transudative pleural effusion is caused by diseases of heart, liver, or kidney, such as heart failure, liver cirrhosis, and kidney failure. However, the present invention is not limited thereto. Exudative pleural effusion is usually associated with cancers, infectious diseases, or autoimmune diseases, such as lung cancers, stomach cancers, breast cancers, lymphoma cancers and other cancers; pulmonary tuberculosis; systemic lupus erythematosus (SLE), and rheumatoid arthritis (RA). However, the present invention is not limited thereto.

The present invention is not restrictive of the method for decocting Chinese medicine, and it can be implemented in any known manner. The present invention is not restrictive of the method for heating the Chinese medicine, and it can be implemented by any known method, such as direct heating and double-boiling.

In the present invention, the term "treat" or "treatment" used herein includes alleviating, relieving, or improving associated symptoms, or inhibiting or controlling the disease progression. However, the present invention is not limited thereto.

In the present invention, the term "effective amount" used herein refers to a necessary dose leading to expected therapeutic effects in a subject treated, and it may vary depending on the route of administration, the use of excipients and the combined use with other medicaments.

The Chinese medicine composition of the present invention may be administered via oral administration or injection.

The Chinese medicine composition of the present invention may further comprise pharmaceutically acceptable carrier, stabilizer, thinner, dispersant, suspending agent, thickener, excipient or the combination thereof.

In the present invention, the term "acceptable" used herein means that it should be compatible with the Chinese medicine composition, preferably be able to stabilize the Chinese medicine composition, and cannot jeopardize the subject treated.

The present invention can achieve the object of treating pleural effusion by administrating a specific Chinese medicine composition to the patient. In addition, surgical operations are not necessary for the therapeutic method of the present invention, preventing the related side effects or complications caused by the surgery, such as sepsis, pneumothorax, and hemothorax.

DETAILED DESCRIPTION OF THE PREFERRED EMBODIMENT

The following embodiments are meant to explain the implementation of the present invention, they should be construed as descriptive merely, and should not restrict the remaining part of the present invention. The person having ordinary skills in the art can easily understand other advantages and effects of the present invention. The present invention may also be implemented or applied by other different embodiments, and various details in this specification may also be modified and changed according to different viewpoints and applications without departing from the spirit of the invention.

Moreover, the ordinal numbers, such as "first" and "second", used to describe the claimed species in the present specification and claims are meant to distinguish a plurality of species having the same name, rather than imply and represent that there is essentially a level, a rank, an executing order, or an manufacturing order among the species, except otherwise specified.

The preparation of the Chinese medicine composition of the present invention is described below, wherein all the materials used herein are commercial and the part by weight is 3.75 gram per part.

Preparation Example 1: Preparation of Chinese Medicine Composition-1

Ten parts by weight of *Poria*, 8 parts by weight of *Polyporus*, 10 parts by weight of *Rhizoma Alismatis*, 5 parts by weight of *Atractylodis Rhizoma,* 5 parts by weight of *Pimenta officinalis,* 3 parts by weight of *Zingiberis Rhizoma,* 3 parts by weight of *Aconiti Lateralis Radix Praeparata,* 3 parts by weight of *Phellodendron amurense,* 2 parts by weight of *Angelica sinensis,* 10 parts by weight of *Astragalus Membranaceus,* 5 parts by weight of *Stephaniae Tetrandrae Radix,* 8 parts by weight of *Descurainiea Semen,* 2 parts by weight of *Ephedra Sinica,* 3 parts by weight of *Armeniacae Semen amarum,* 3 parts by weight of *Ginseng Radix et Rhizoma,* 3 parts by weight of *Anredera Cordifolia* and 1 parts by weight of *Velvet Antler* were provided to form a first mixture-1; the first mixture-1 was mixed with about 400 parts by weight of water to form a second mixture-1; the second mixture-1 was heated for about 1 hour to obtain a crude extract of about 106 parts by weight; and, the crude extract was filtered to obtain the Chinese Medicine Composition-1.

Preparation Example 2: Preparation of Chinese Medicine Composition-2

Fifteen parts by weight of *Poria,* 8 parts by weight of *Polyporus,* 15 parts by weight of *Rhizoma Alismatis,* 5 parts by weight of *Atractylodis Rhizoma,* 5 parts by weight of *Pimenta Officinalis,* 3 parts by weight of *Zingiberis Rhizoma,* 3 parts by weight of *Aconiti Lateralis Radix Praeparata,* 3 parts by weight of *Phellodendron amurense,* 2 parts by weight of *Angelica sinensis,* 15 parts by weight of *Astragalus Membranaceus,* 8 parts by weight of *Stephaniae Tetrandrae Radix,* 15 parts by weight of *Descurainiea Semen,* 2 parts by weight of *Ephedra Sinica,* 3 parts by weight of *Armeniacae Semen amarum,* 5 parts by weight of *Ginseng Radix et Rhizoma,* 3 parts by weight of *Anredera Cordifolia* and 1 parts by weight of *Velvet Antler* were provided to form a second mixture-2; the first mixture-2 was mixed with about 400 parts by weight of water to form a second mixture-2; the second mixture-2 was heated for about 1 hour to obtain a crude extract of about 107 parts by weight; and, the crude extract was filtered to obtain the Chinese Medicine Composition-2.

Preparation Example 3: Preparation of Chinese Medicine Composition-3

Twenty parts by weight of *Poria,* 8 parts by weight of *Polyporus,* 20 parts by weight of *Rhizoma Alismatis,* 5 parts by weight of *Atractylodis Rhizoma,* 5 parts by weight of *Pimenta Officinalis,* 3 parts by weight of *Zingiberis Rhizoma,* 3 parts by weight of *Aconiti Lateralis Radix Praeparata,* 3 parts by weight of *Phellodendron amurense,* 2 parts by weight of *Angelica sinensis,* 20 parts by weight of *Astragalus Membranaceus,* 10 parts by weight of *Stephaniae Tetrandrae Radix,* 20 parts by weight of *Descurainiea Semen,* 2 parts by weight of *Ephedra Sinica,* 3 parts by weight of *Armeniacae Semen amarum,* 8 parts by weight of *Ginseng Radix et Rhizoma,* 3 parts by weight of *Anredera Cordifolia* and 1 parts by weight of *Velvet Antler* were provided to form a second mixture-3; the first mixture-3 was mixed with about 400 parts by weight of water to form a second mixture-3; the second mixture-3 was heated for about 1 hour to obtain a crude extract of about 107 parts by weight; and, the crude extract was filtered to obtain the Chinese Medicine Composition-3.

Example 1

The patient of Example 1 was a male with a body weight of about 65 kilograms. Sudden physical discomfort and rapid heartbeat were found in the patient, and X-ray examination was performed on the patient with the results that a white fog showed in the chest and CRP was 30.8 mg/dL (normal value is less than 1 mg/dL). More examinations were performed on the patient, so that lung cancer was ruled out and pneumonia was suspected. Pleural effusion was recurrent, the extraction of pleural effusion was performed every 3 to 5 days, and the extraction amount was about 800 cc each time. However, the pleural was still recurrent.

A treatment of the present invention applied to the patient of Example 1 was described below: a daily dose of the Chinese medicine composition-1 was administered to the patient every day from the first day. On the first day, the drainage of the right-sided pleural effusion was about 650 cc, the urine output was about 1000 cc, and the body weight was 74.5 kg. On the second day, the drainage of the right-sided pleural effusion was about 800 cc, and the body weight was 72.3 kg. On the third day, the drainage of the right-sided pleural effusion was about 675 cc, and the urine output was about 2000 cc. On the fourth day, the drainage of the right-sided pleural effusion was about 550 cc, the urine output was about 2000 cc, and the body weight was 71.5 kg. On the fifth day, the drainage of the right-sided pleural effusion was about 430 cc, the urine output was about 2000 cc, and the body weight was 71.3 kg. On the sixth day, the drainage of the right-sided pleural effusion was about 170 cc, the urine output was about 2000 cc, and the body weight was 71.1 kg. On the seventh day, the drainage of the right-sided pleural effusion was about 20 cc, and the body weight was 70.6 kg After the administration of the Chinese medicine composition-1, the drainage of the right-sided pleural effusion decreased from 650 cc of the first day to 20 cc of the seventh day, the urine output increased, and the weight loss was slowed down, indicating that the situation of the pleural effusion was significantly improved.

Example 2

The patient of Example 2 was a male about 80 years old, with a slight edema of the feet, and was diagnosed as pulmonary tuberculosis through X-ray and other examinations. Left- and right-sided pleural effusions was recurrent during the period of treating pulmonary tuberculosis, the drainage or extraction of pleural effusion was performed every day, and the drainage or extraction amount was about 500 cc each time. However, the pleural effusion was still recurrent.

A treatment of the present invention applied to the patient of Example 2 was described below: a daily dose of the Chinese medicine composition-2 was administered to the patient every day. On the first day, the extracted amount of the left-sided pleural effusion was about 570 cc, the drainage of right-sided pleural effusion was about 5 cc, the urine output was about 2000 cc, and the body weight was about 70.4 kg. On the second day, the drainage of right-sided pleural effusion was 0 cc. On the third day, the drainage of right-sided pleural effusion was 0 cc, the urine output was about 2000 cc, and the body weight was about 70.3 kg. On the fourth day, the drainage of right-sided pleural effusion was 0 cc, the urine output was about 2000 cc, and the body weight was about 70.7 kg. On the fifth day, the drainage tube was removed, the urine output was about 1900 cc, and the body weight was about 70.6 kg.

After the administration of Chinese medicine composition-2 for 5 days, the left- and right-sided pleural effusions are significantly reduced, the drainage tube was removed after the fifth day, and the drainage of pleural effusion was not performed from the second day to the fifth day during the treatment. Therefore, the present invention was able to significantly improve the condition of pleural effusion.

Example 3

The patient of Example 3 was a male over 75 years old, weighing about 66 kg, diagnosed as pulmonary tuberculosis. Left- and right-sided pleural effusions were recurrent during the period of treating pulmonary tuberculosis, and the extraction of pleural effusion was performed every 2 to 3 days.

A treatment of the present invention applied to the patient of Example 3 was described below: a daily dose of the Chinese medicine composition-3 was administered to the patient every day from the first day. On the first day, the left-sided pleural effusion was extracted for about 600 cc, the urine output was about 1700 cc, and the body weight was about 71.2 kg. On the second day, the urine output was about 2300 cc, and the body weight was about 70.6 kg. On the third day, the right-sided pleural effusion was extracted for about 500 cc, the urine output was about 2400 cc, and the body weight was about 69.8 kg. On the fourth day, the urine output was about 2500 cc, and the body weight was about 67.7 kg. On the fifth day, the urine output was about 2700 cc, and the body weight was about 67.6 kg. On the sixth day, the urine output was about 1700 cc, and the body weight was about 66.8 kg. On the seventh day, the urine output was about 1900 cc, and the body weight was about 67.2 kg. On the eighth day, the urine output was about 2100 cc, and the body weight was about 67.8 kg. On the ninth day, the urine output was about 1700 cc, and the body weight was about 67.9 kg. On the tenth day, the urine output was about 1900 cc, and the body weight was about 68.3 kg. On the eleventh day, the patient was discharged from the hospital and observed for more than 3 months after the discharge. There was no recurrence of pleural effusion or foot edema.

After the administration of Chinese medicine composition-3 for about ten days, during which the extraction of pleural effusion was performed twice only, the urine output was back to normal, and the body weigh was maintained at about 68 kg, indicating the condition of pleural diffusion was significantly improved. In addition, there was no recurrence of pleural effusion after more than 3 months of follow-up observation.

Although the present invention has been explained in relation to its preferred embodiment, it is to be understood that many other possible modifications and variations can be made without departing from the spirit and scope of the invention as hereinafter claimed.

What is claimed is:

1. A method for treating pleural effusion, comprising:
administering a Chinese medicine composition to a subject in need thereof; wherein, the Chinese medicine composition is an extract of a first mixture comprising consisting of 8-22 parts by weight of *Poria*, 6-10 parts by weight of *Polyporus*, 8-22 parts by weight of *Rhizoma Alismatis*, 3-7 parts by weight of *Atractylodis Rhizoma*, 3-7 parts by weight of *Pimenta officinalis*, 1-5 parts by weight of *Zingiberis Rhizoma*, 1-5 parts by weight of *Aconiti Lateralis Radix praeparata*, 1-5 parts by weight of *Phellodendron amurense*, 0.5-4 parts by weight of *Angelica sinensis*, 8-22 parts by weight of *Astragalus membranaceus*, 3-12 parts by weight of *Stephaniae Tetrandrae Radix*, 6-22 parts by weight of *Descurainiea Semen*, 0.5-4 parts by weight of *Ephedra*

*sinica*, 1-5 parts by weight of *Armeniacae Semen amarum*, 1-10 parts by weight of *Ginseng radix* et *Rhizoma*, 1-5 parts by weight of *Anredera cordifolia* and 0.1-3 parts by weight of *Velvet Antler;*
wherein the Chinese medicine composition is prepared by the following steps:
providing the first mixture;
mixing the first mixture with water to form a second mixture;
heating the second mixture to obtain the Chinese medicine composition.

2. The method of claim 1, wherein the first mixture consists of 9-21 parts by weight of *Poria*, 7-9 parts by weight of *Polyporus*, 9-21 parts by weight of *Rhizoma alismatis*, 4-6 parts by weight of *Atractylodis Rhizoma*, 4-6 parts by weight of *Pimenta officinalis*, 2-4 parts by weight of *Zingiberis Rhizoma*, 2-4 parts by weight of *Aconiti Lateralis Radix praeparata*, 2-4 parts by weight of *Phellodendron amurense*, 1-3 parts by weight of *Angelica sinensis*, 9-21 parts by weight of *Astragalus membranaceus*, 4-11 parts by weight of *Stephaniae Tetrandrae Radix*, 7-21 parts by weight of *Descurainiea Semen*, 1-3 parts by weight of *Ephedra sinica*, 2-4 parts by weight of *Armeniacae Semen amarum*, 2-9 parts by weight of *Ginseng radix* et *Rhizoma*, 2-4 parts by weight of *Anredera cordifolia* and 0.5-2 parts by weight of *Velvet Antler.*

3. The method of claim 1, wherein the first mixture consists of 8-12 parts by weight of *Poria*, 6-10 parts by weight of *Polyporus*, 8-12 parts by weight of *Rhizoma alismatis*, 3-7 parts by weight of *Atractylodis Rhizoma*, 3-7 parts by weight of *Pimenta officinalis*, 1-5 parts by weight of *Zingiberis Rhizoma*, 1-5 parts by weight of *Aconiti Lateralis Radix praeparata*, 1-5 parts by weight of *Phellodendron amurense*, 0.5-4 parts by weight of *Angelica sinensis*, 8-12 parts by weight of *Astragalus membranaceus*, 3-7 parts by weight of *Stephaniae Tetrandrae Radix*, 6-10 parts by weight of *Descurainiea Semen*, 0.5-4 parts by weight of *Ephedra sinica*, 1-5 parts by weight of *Armeniacae Semen amarum*, 1-5 parts by weight of *Ginseng radix* et *Rhizoma*, 1-5 parts by weight of *Anredera cordifolia* and 0.1-3 parts by weight of *Velvet Antler.*

4. The method of claim 3, wherein the first mixture consists of 9-11 parts by weight of *Poria*, 7-9 parts by weight of *Polyporus*, 9-11 parts by weight of *Rhizoma Alismatis*, 4-6 parts by weight of *Atractylodis Rhizoma*, 4-6 parts by weight of *Pimenta officinalis*, 2-4 parts by weight of *Zingiberis Rhizoma*, 2-4 parts by weight of *Aconiti Lateralis Radix praeparata*, 2-4 parts by weight of *Phellodendron amurense*, 1-3 parts by weight of *Angelica sinensis*, 9-11 parts by weight of *Astragalus membranaceus*, 4-6 parts by weight of *Stephaniae Tetrandrae Radix*, 7-9 parts by weight of *Descurainiea Semen*, 1-3 parts by weight of *Ephedra sinica*, 2-4 parts by weight of *Armeniacae Semen amarum*, 2-4 parts by weight of *Ginseng radix* et *Rhizoma*, 2-4 parts by weight of *Anredera cordifolia* and 0.5-2 parts by weight of *Velvet Antler.*

5. The method of claim 1, wherein the first mixture consists of 13-17 parts by weight of *Poria*, 6-10 parts by weight of *Polyporus*, 13-17 parts by weight of *Rhizoma Alismatis*, 3-7 parts by weight of *Atractylodis Rhizoma*, 3-7 parts by weight of *Pimenta officinalis*, 1-5 parts by weight of *Zingiberis Rhizoma*, 1-5 parts by weight of *Aconiti Lateralis Radix praeparata*, 1-5 parts by weight of *Phellodendron amurense*, 0.5-4 parts by weight of *Angelica Sinensis*, 13-17 parts by weight of *Astragalus membranaceus*, 6-10 parts by weight of *Stephaniae Tetrandrae Radix*, 13-17 parts by weight of *Descurainiea Semen*, 0.5-4 parts by weight of

*Ephedra sinica,* 1-5 parts by weight of *Armeniacae Semen Amarum,* 3-7 parts by weight of *Ginseng radix* et *Rhizoma,* 1-5 parts by weight of *Anredera cordifolia* and 0.1-3 parts by weight of *Velvet Antler.*

6. The method of claim 5, wherein the first mixture consists of 14-16 parts by weight of *Poria,* 7-9 parts by weight of *Polyporus,* 14-16 parts by weight of *Rhizoma Alismatis,* 4-6 parts by weight of *Atractylodis Rhizoma,* 4-6 parts by weight of *Pimenta officinalis,* 2-4 parts by weight of *Zingiberis Rhizoma,* 2-4 parts by weight of *Aconiti Lateralis Radix praeparata,* 2-4 parts by weight of *Phellodendron amurense,* 1-3 parts by weight of *Angelica sinensis,* 14-16 parts by weight of *Astragalus membranaceus,* 14-16 parts by weight of *Stephaniae Tetrandrae Radix,* 14-16 parts by weight of *Descurainiea Semen,* 1-3 parts by weight of *Ephedra sinica,* 2-4 parts by weight of *Armeniacae Semen amarum,* 4-6 parts by weight of *Ginseng radix* et *Rhizoma,* 2-4 parts by weight of *Anredera cordifolia* and 0.5-2 parts by weight of *Velvet Antler.*

7. The method of claim 1, wherein the first mixture consists of 18-22 parts by weight of *Poria,* 6-10 parts by weight of *Polyporus,* 18-22 parts by weight of *Rhizoma alismatis,* 3-7 parts by weight of *Atractylodis Rhizoma,* 3-7 parts by weight of *Pimenta officinalis,* 1-5 parts by weight of *Zingiberis Rhizoma,* 1-5 parts by weight of *Aconiti Lateralis Radix praeparata,* 1-5 parts by weight of *Phellodendron*

*amurense,* 0.5-4 parts by weight of *Angelica sinensis,* 18-22 parts by weight of *Astragalus membranaceus,* 8-12 parts by weight of *Stephaniae Tetrandrae Radix,* 18-22 parts by weight of *Descurainiea Semen,* 0.5-4 parts by weight of *Ephedra sinica,* 1-5 parts by weight of *Armeniacae Semen amarum,* 6-10 parts by weight of *Ginseng radix* et *Rhizoma,* 1-5 parts by weight of *Anredera cordifolia* and 0.1-3 parts by weight of *Velvet Antler.*

8. The method of claim 7, wherein the first mixture consists of 19-21 parts by weight of *Poria,* 7-9 parts by weight of *Polyporus,* 19-21 parts by weight of *Rhizoma Alismatis,* 4-6 parts by weight of *Atractylodis Rhizoma,* 4-6 parts by weight of *Pimenta Officinalis,* 2-4 parts by weight of *Zingiberis Rhizoma,* 2-4 parts by weight of *Aconiti Lateralis Radix praeparata,* 2-4 parts by weight of *Phellodendron amurense,* 1-3 parts by weight of *Angelica* Sinesis, 19-21 parts by weight of *Astragalus membranaceus,* 9-11 parts by weight of *Stephaniae Tetrandrae Radix,* 19-21 parts by weight of *Descurainiea Semen,* 1-3 parts by weight of *Ephedra sinica,* 2-4 parts by weight of *Armeniacae Semen amarum,* 7-9 parts by weight of *Ginseng radix* et *Rhizoma,* 2-4 parts by weight of *Anredera cordifolia* and 0.5-2 parts by weight of *Velvet Antler.*

9. The method of claim 1, wherein each of parts by weight is 2.5-5 grams per part.

* * * * *